US008177830B2

(12) United States Patent
Sutermeister et al.

(10) Patent No.: US 8,177,830 B2
(45) Date of Patent: May 15, 2012

(54) ROTATABLE CATHETER ASSEMBLY

(75) Inventors: Derek C. Sutermeister, Eden Prairie, MN (US); Jay T. Rassat, Buffalo, MN (US); James M. Anderson, Fridley, MN (US); Benjamin Y. Arcand, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 18 days.

(21) Appl. No.: 12/848,805

(22) Filed: Aug. 2, 2010

(65) Prior Publication Data
US 2010/0298923 A1    Nov. 25, 2010

Related U.S. Application Data

(62) Division of application No. 12/156,039, filed on May 29, 2008, now abandoned.

(51) Int. Cl.
*A61F 2/06* (2006.01)
(52) U.S. Cl. .................................... 623/1.11
(58) Field of Classification Search .......... 604/96.01, 604/99.01; 606/191, 192, 193, 194, 195; 623/1.11
See application file for complete search history.

(56) References Cited

U.S. PATENT DOCUMENTS

| 7,695,452 | B2 | 4/2010 | Lenker |
| 2002/0072755 | A1 | 6/2002 | Bigus et al. |
| 2003/0055483 | A1 | 3/2003 | Gumm |
| 2005/0154442 | A1 | 7/2005 | Eidenschink et al. |
| 2005/0187602 | A1 | 8/2005 | Eidenschink |
| 2006/0206188 | A1 | 9/2006 | Weber et al. |

FOREIGN PATENT DOCUMENTS

| EP | 0492361 | 1/1992 |
| WO | 2005082280 | 9/2005 |
| WO | 2006020457 | 2/2006 |

OTHER PUBLICATIONS

International Search Report (10 pgs.) Oct. 1, 2009.

*Primary Examiner* — Ryan Severson
*Assistant Examiner* — Jonathan W Miles
(74) *Attorney, Agent, or Firm* — Brooks, Cameron & Huebsch, PLLC

(57) ABSTRACT

Embodiments of the present disclosure include methods and systems for a catheter assembly including a catheter shaft, a balloon positioned on the catheter shaft, where the balloon has a first balloon waist, a first lead extending longitudinally through the catheter shaft, and a first sealing member adjacent the first balloon waist and coupled to the first lead, where the first lead can provide electrical current to reversibly transition the first sealing member from a nonactivated state to an activated state in response to a temperature change in the first sealing member, and where at least a portion of the balloon rotates relative the catheter shaft in the nonactivated state and the first sealing member engages the first balloon waist to form a fluid tight seal and to prevent rotation of the balloon relative the catheter shaft in the activated state.

20 Claims, 13 Drawing Sheets

ROTATABLE CATHETER ASSEMBLY

CROSS-REFERENCE TO RELATED APPLICATIONS

This application is a divisional of U.S. patent application Ser. No. 12/156,039, filed May 29, 2008, which is incorporated herein by reference in its entirety.

TECHNICAL FIELD

The present disclosure relates generally to assemblies and methods for their use, and more particularly, their use with stents.

BACKGROUND

Stent systems can be widely used in the treatment of stenoses. For example, intravascular stents can be used in coronary, renal, and carotid arteries to maintain an open passage through the artery. The intravascular stent can be positioned in a clogged artery, for example, by a catheter and set in place by inflating a balloon upon which the stent is mounted. Inflating the balloon expands the diameter of the stent and opens the previously clogged artery. The balloon can then be deflated and removed from the patient while the stent retains an open passage through the artery.

In some instances a vessel can be bifurcated, i.e., a side branch passage is connected to the vessel, at the treatment site. Despite efforts to use a stent at such bifurcations, the sites can be inadequately treated by a stent due to improper placement and subsequent obstruction of the side branch passage.

In delivering a stent to a vessel location, many current devices rely on either passive torque (e.g., pushing the stent forward and allowing the stent that is fixed on the guidewire/balloon to passively rotate itself into place) or creating torque from outside of the patient to properly orient the medical device in the passage.

Unfortunately, such devices often require a significant portion of the catheter assembly, in addition to the balloon, to be subjected to torque in order to align the stent. Also, stent delivery systems for deployment of one or more stent bodies at or around a vessel bifurcation can have difficulties aligning a stent relative to the side branch at the bifurcation of the primary and secondary passages. Subjecting the catheter as well as a vessel to such extraneous torque can cause damage to the stent, the delivery system, and/or the vessel itself.

DETAILED DESCRIPTION

Figure 1:
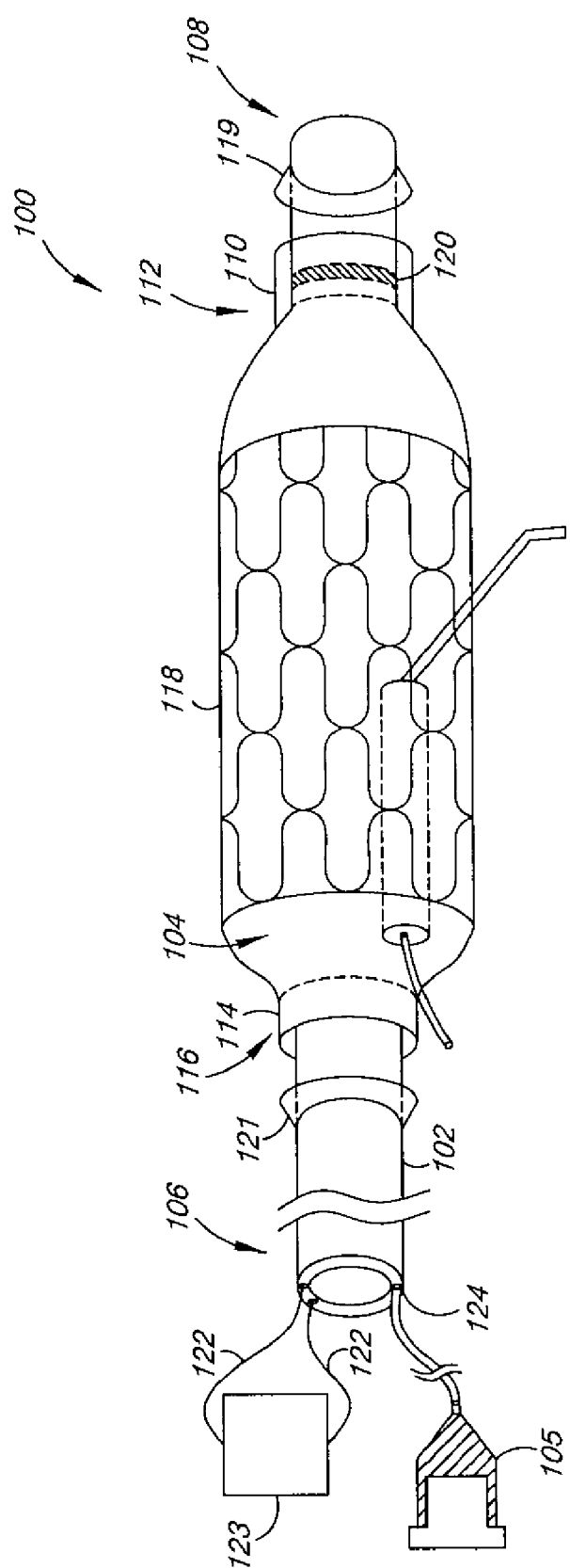
FIG. 1 illustrates a plan view of a catheter assembly according to various embodiments of the present disclosure.

Embodiments of the present disclosure are directed to a catheter assembly and methods for their use that are capable of allowing a medical device such as a stent to be maneuvered and aligned at a vessel bifurcation or other location without the need to torque or rotate the entire catheter shaft in order to align the stent at a vessel bifurcation. Various devices and methods described herein provide a catheter assembly with a rotatable balloon about which a stent may be mounted on or engaged to. The rotatable balloon can be at least partially rotatable relative to the catheter shaft, thereby eliminating the need to apply torque to the catheter shaft to align the stent at a vessel bifurcation.

As used herein, the term "stent" refers to an expandable prosthesis for implantation into a body lumen or vessel and includes devices such as stents, grafts, stent-grafts, vena cava filters, etc. In some embodiments, a stent may be at least partially constructed of a variety of materials such as stainless steel, nickel, titanium, nitinol, platinum, gold, chrome, and cobalt, as well as other metals and their combinations and/or alloys.

A stent may also be at least partially constructed of a polymer material. The stent may also be at least partially constructed of a shape-memory polymer or material. The stent can be balloon expandable, self-expandable, hybrid expandable, or a combination thereof. In some embodiments, a stent may include one or more areas, bands, coatings, and/or members that are detectable by imaging modalities such as X-ray, magnetic resonance imaging (MRI), or ultrasound. In various embodiments, at least a portion of the stent can be at least partially radiopaque. In addition, in some embodiments, a stent may include one or more therapeutic and/or lubricious coatings applied thereto.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide any number of additional embodiments. In addition, as will be appreciated, the proportion and the relative scale of the elements provided in the figures are intended to illustrate the embodiments of the present invention, and should not be taken in a limiting sense.

FIG. 1 illustrates a plan view of a catheter assembly 100 according to embodiments of the present disclosure. As shown in FIG. 1, the catheter assembly 100 includes a catheter shaft 102 and a balloon 104 positioned on the catheter shaft 102.

The catheter shaft 102 can be an elongate body having a lumen that extends between and through a proximal end 106 and distal end 108. The elongate body can allow for passage of, for example, a guidewire and/or inflation fluid, among other components of the catheter assembly 100.

The balloon 104 positioned on the catheter shaft 102 can be an angioplasty balloon, a stent delivery balloon, or other inflatable member which can be used or incorporated into a catheter assembly 100. The balloon 104 can be inflated with an inflation fluid delivered through an inflation lumen 124 from, for example, a syringe 105.

The balloon 104 includes a first balloon waist 110 located at a first end 112 of the balloon 104 and a second balloon waist 114 located at a second end 116 of the balloon 104, where the balloon body 118 extends therebetween.

In FIG. 1, the first balloon waist 110 is illustrated as the distal balloon waist, however, the present disclosure includes embodiments where the first balloon waist 110 is the proximal balloon waist.

In some embodiments, the wall thickness of the first balloon waist 110 and second balloon waist 114 can be thicker than the thickness of the balloon body 118. In some embodiments, the thickness of the first balloon waist 110 and/or the second balloon waist 114 can be approximately twice that of the balloon body 118 and approximately ten (10) times more resistant to radial pressures. By including a balloon 104 where the first balloon waist 110 and/or second balloon waist 114 are more resistant to radial pressures, the balloon body 118 can expand more readily when inflation fluid is introduced into the balloon 104, while the first and/or second balloon waists 110, 114 can be more likely to keep a fluid tight seal with a sealing member, as discussed further herein.

In some embodiments, the first and/or second balloon waists 110, 114 can be reinforced. For example, the first and/or second balloon waists 110, 114 can be supplemented with one or layers of material. The layers of material can be external to the first and/or second balloon waists 110, 114, so that the layers can reinforce the first and/or second balloon waists 110, 114 to help improve the rotational characteristics of the balloon 104. In such embodiments the layer may be constructed of one or more strands of fiber or layers of stainless steel or other suitable reinforcing material.

In addition, the balloon 104 can be constructed of a suitable balloon material known to those of skill in the art, for example, thermoplastic elastomeric and nonelastomeric polymers and thermosets including moisture curable polymers.

Examples of suitable balloon 104 materials include, but are not limited to, polyolefins, polyesters, polyurethanes, polyamides, polyimides, polycarbonates, polyphenylene sulfides, polyphenylene oxides, polyethers, silicones, polycarbonates, styrenic polymers, copolymers thereof, and mixtures thereof. Other balloon 104 materials are also possible.

In order to allow at least a portion of the balloon 104 to rotate freely relative to the catheter shaft 102, at least a portion of the balloon 104 is not attached to the catheter shaft 102. In embodiments of the present disclosure, the first waist 110 is adjacent a first sealing member 120, where the first sealing member 120 can reversibly transition between an activated state and a nonactivated state. As discussed herein, in the nonactivated state at least a portion of the balloon 104 rotates relative the catheter shaft 102, while in the activated state, the first sealing member 120 engages the first balloon waist 110 to fowl a fluid tight seal and to prevent rotation of the balloon 104 relative the catheter shaft 102.

The catheter assembly 100 also includes a first lead 122 extending longitudinally through the catheter shaft 102. The first lead 122 can be a conductive wire or member of gold, gold plated stainless steel, silver coated stainless steel, and/or Elgiloy, among other conductive materials. The first lead 122 can extend from a current source 123 to the first sealing member 120 through or adjacent to the catheter shaft 102. The current source 123 can be, for example, a battery, or a switch, similar to a light switch.

In some embodiments, the first lead 122 can be in the form of an insulated wire or other member which engages the first sealing member 120 via an exposed end which extends through an opening in the catheter shaft 102. Such a lead may be co-extruded with one or more catheter shafts 102 and/or the balloon 104. A proximal end of the first lead 122 can be engaged to a current source which can be activated to transmit the current through the first lead 122 to the first sealing member 120 when desired. In various embodiments, the first lead 122 is at least partially contained within one or more lumens defined by the catheter shaft 102. A distal end of the first lead 122 can close the electric current by extending through the catheter shaft 102 to the current source 123.

In embodiments of the present disclosure, the first lead 122 is coupled to the first sealing member 120 and allows for an electric current to be delivered to the first sealing member 120. The electric current delivered through the first lead 122 causes a temperature change in the first sealing member 120 that causes the first sealing member 120 to expand and/or contract. As such, at least a portion of the first sealing member 120 can be formed of a material that can expand or contract in response to a temperature change. In some embodiments, the first sealing member 120 can be formed of metal, and/or metal-alloys such as nickel-titanium alloys, (e.g., Nitinol), copper-zinc-aluminum alloys, and/or copper-aluminum-nickel alloys.

In some embodiments, the temperature change in the first sealing member 120 can be a temperature increase to expand the first sealing member 120. In various embodiments, the first sealing member 120 can contract in response to the temperature change. For example, in some embodiments the first sealing member 120 can transition between solid state phases in response to a temperature change, where one solid state phase is the nonactivated state, and the second solid state phase is the activated state. For example, the solid state phase change can occur with a temperature change of approximately ten (10) degrees Celsius. Other configurations are also possible.

As discussed herein, in some embodiments, the first sealing member 120 can be formed of a shape memory alloy (e.g., Nitinol). As one skilled in the art will appreciate, the two solid state phases, which occur in shape memory alloys, are martensite and austenite. At room temperature, the shape memory alloy can be in the martensite phase. The first sealing member 120 in this phase can be deformed since the metal atoms easily slide past one another. Heating the first sealing member 120 changes the first sealing member 120 to the rigid austenite phase. Upon cooling, the first sealing member 120 formed of a shape memory alloy will return to the martensite phase, but will retain its shape until pressure is applied.

As a result of forming the first sealing member 120 of a material that can expand and/or contract in response to a temperature change, the first sealing member 120 can be formed to have a pre-current shape, or nonactivated state, and a post-current shape, or activated shape, that is different or, in some instances, larger, than the pre-current shape.

As used herein, "pre-current" or "non-activated" refers to the condition of the first sealing member 120 before the first sealing member 120 is exposed to an electric current sufficient to cause a temperature change in the first sealing member 120. As used herein, "post-current" or "activated" refers to the condition of the first sealing member 120 when the first sealing member 120 is being exposed to the electric current sufficient to cause the temperature change in the first sealing member 120.

As illustrated in FIG. 1, the catheter can be equipped with one or more hubs, tips, rings, or other devices 119, 121 which may abut the first sealing member 120 and/or limit the potential for undesired longitudinal migration of the balloon 104 relative to the catheter shaft 102.

Figure 2A:
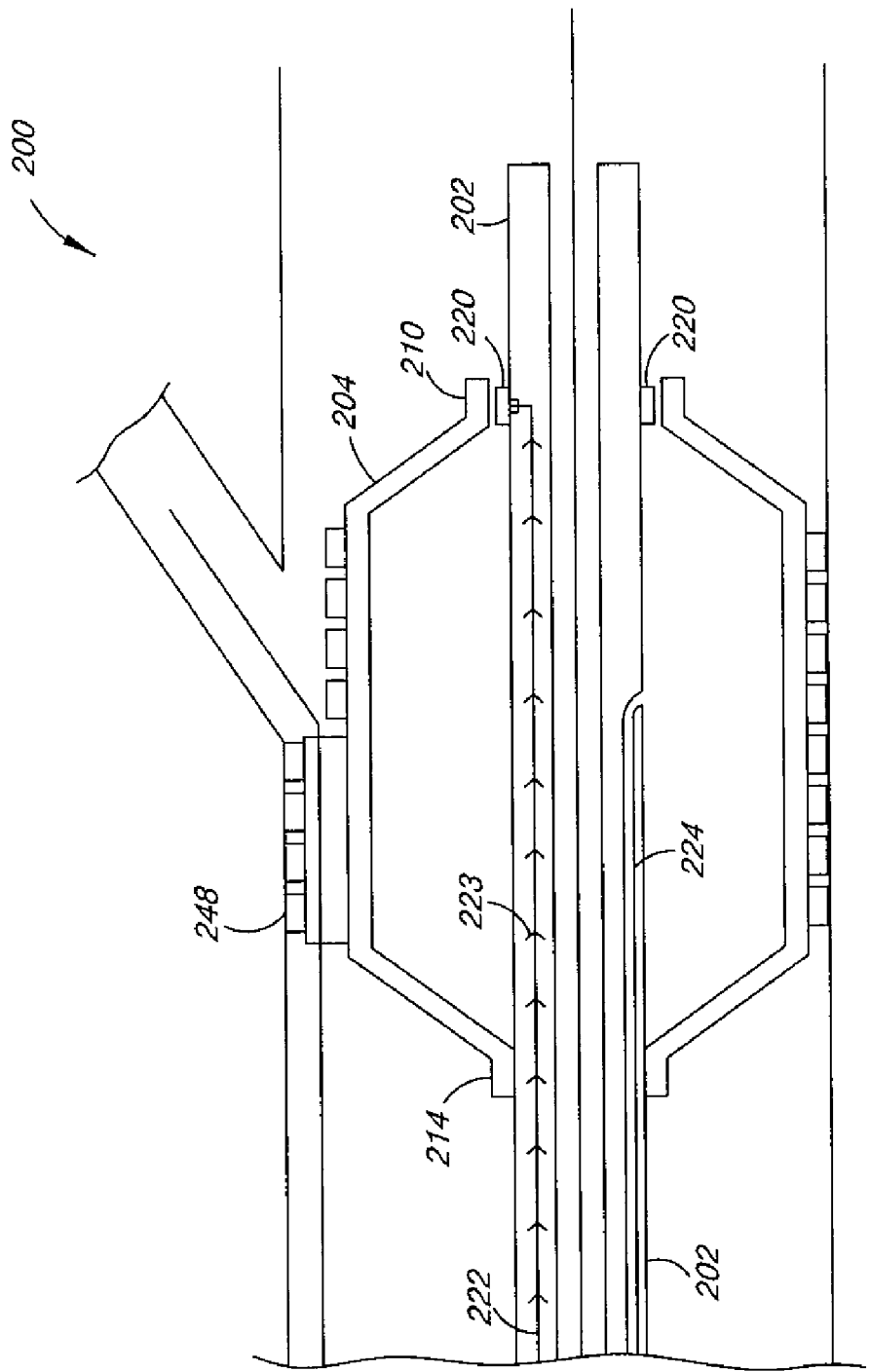
FIGS. 2A and 2B illustrate a cross-sectional view of an embodiment of the catheter assembly according to an embodiment of the present disclosure.
Figure 2B:
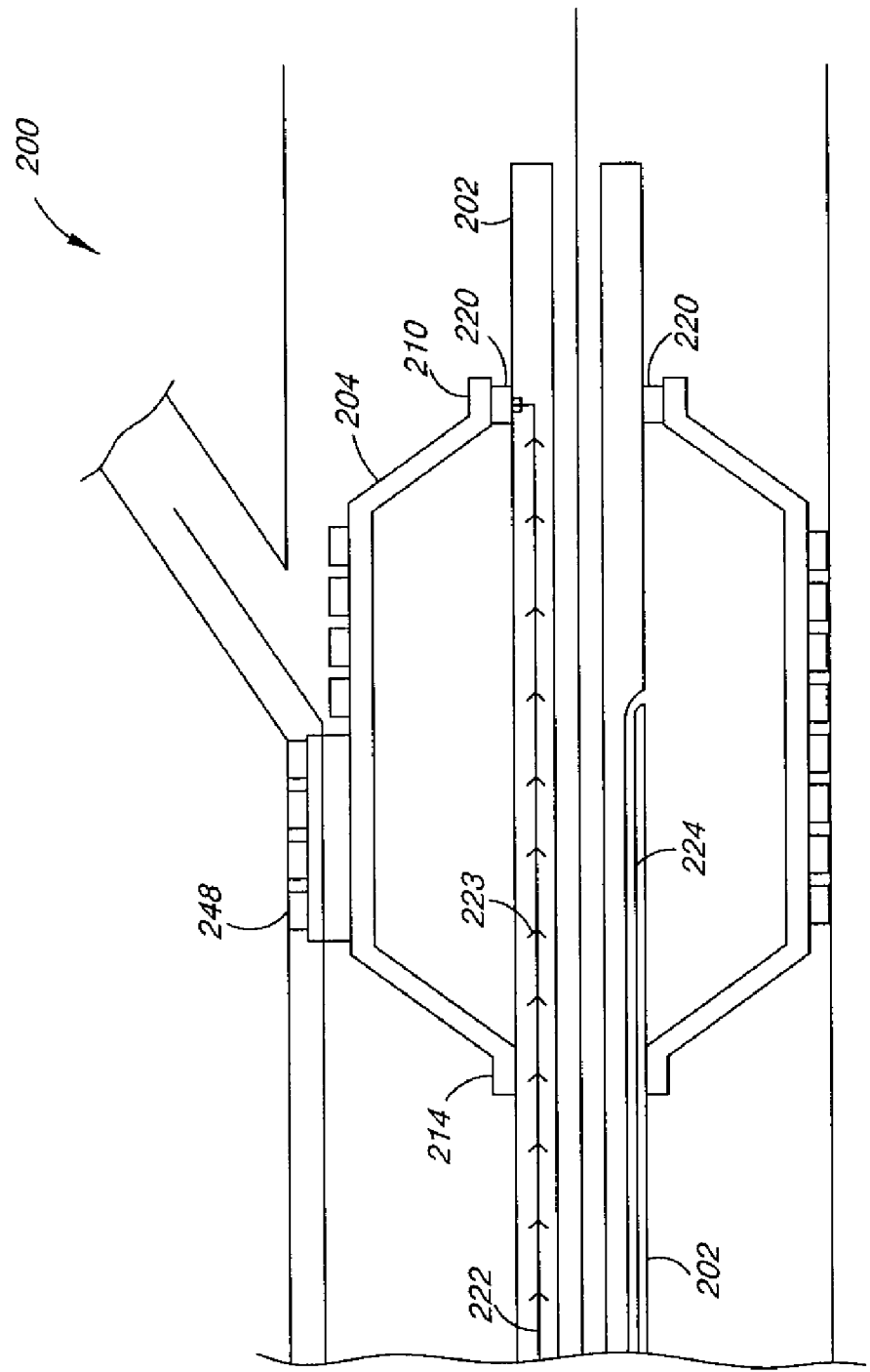

FIGS. 2A and 2B illustrate a cross-sectional view of an embodiment of the catheter assembly 200 including the first sealing member 220 coupled to the catheter shaft 202. FIG. 2A illustrates the first sealing member 220 in the nonactivated state, and FIG. 2B illustrates the first sealing member 220 in the activated state. In embodiments where the first sealing member 220 is coupled to the catheter shaft 202, the first balloon waist 210 can be adjacent the first sealing member 220, however, the first balloon waist 210 can be positioned such that the inner diameter of the first balloon waist 210 can rotate around the catheter shaft 202 when the first sealing member 220 is in the nonactivated state.

As illustrated in FIGS. 2A and 2B, the first sealing member 220 can be coupled to the outside surface of the catheter shaft 202. In some embodiments, the first sealing member 220 can have a ring configuration, encircling the catheter shaft 202.

In some embodiments, the first lead 222 can deliver current, shown by arrows 223, to the first sealing member 220. In FIGS. 2A and 2B, as well as FIGS. 3-7, the first lead 222 is shown connected to at least the first sealing member 220, however, the return path of the first lead 222 is not shown. One skilled in the art will appreciate that the lumen for the first lead extends back through the catheter shaft 202 to a current source, as discussed herein.

In various embodiments, the first lead 222 can be co-extruded with the catheter shaft 202 to provide a lumen for the first lead 222 that is separate from a guidewire lumen and/or inflation lumen. The first lead lumen can also include openings to allow the first lead 222 to be electrically connected to the first sealing member 220.

As the first lead 222 delivers electric current to the first sealing member 220, the temperature of the first sealing member 220 can, for example, increase, causing the first sealing member 220 to transition from a nonactivated state, as shown in FIG. 2A, to an activated state, as shown in FIG. 2B. Once the first sealing member 220 is transitioned into the activated state, the first sealing member 220 can engage the first balloon waist 210 to seal the balloon 204, thereby allowing the balloon 204 to be expanded, for example, by inflation fluid via the inflation lumen 224. In other words, the first sealing member 220 can expand, effectively plugging the first balloon waist 210, to prevent inflation fluid from leaking between the first balloon waist 210 and the first sealing member 220.

In some embodiments, the first sealing member 220 can expand to an outside surface diameter that is approximately 0.5 percent to 20 percent larger than the diameter in the nonactivated state. For example, the first sealing member 220 can have an outside surface diameter of approximately 2 millimeters in the nonactivated state and an outside surface diameter of approximately 2.4 millimeters in the activated state, for a 20 percent increase in diameter.

As shown in FIGS. 2A and 2B, in some embodiments, the balloon 204 includes the second balloon waist 214 fixedly coupled to the catheter shaft 202. As such, a portion of the balloon 204 is rotatable about the catheter shaft 202 when the first sealing member 220 is in the nonactivated state. As illustrated, the portion of the balloon 204 near the first balloon waist 210 can rotate about the catheter shaft 202. In some embodiments, however, the balloon can be fully rotatable about the catheter shaft, as discussed herein.

Figure 3A:
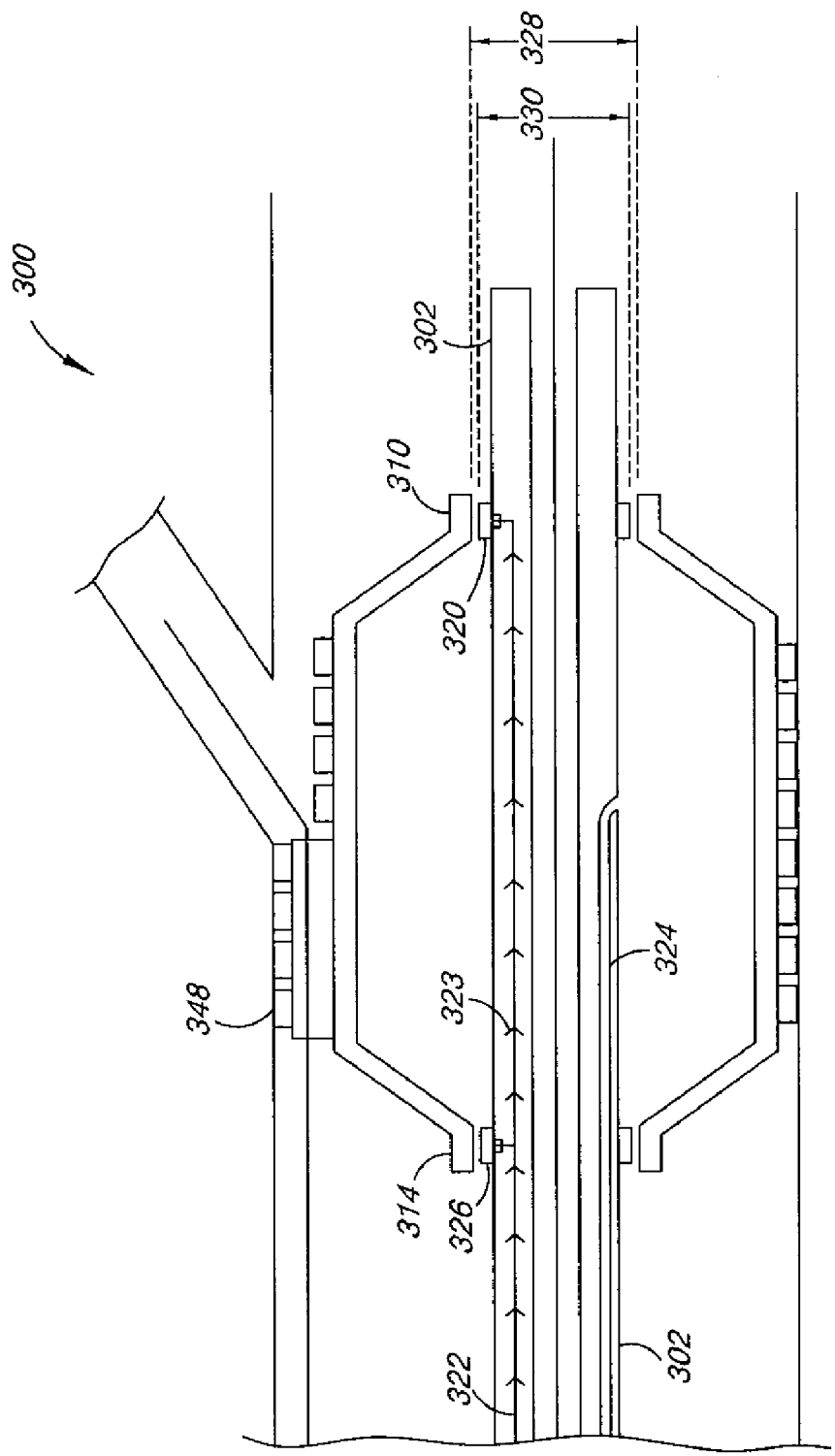
FIGS. 3A and 3B illustrate a cross-sectional view an embodiment of the catheter assembly according to an embodiment of the present disclosure.
Figure 3B:
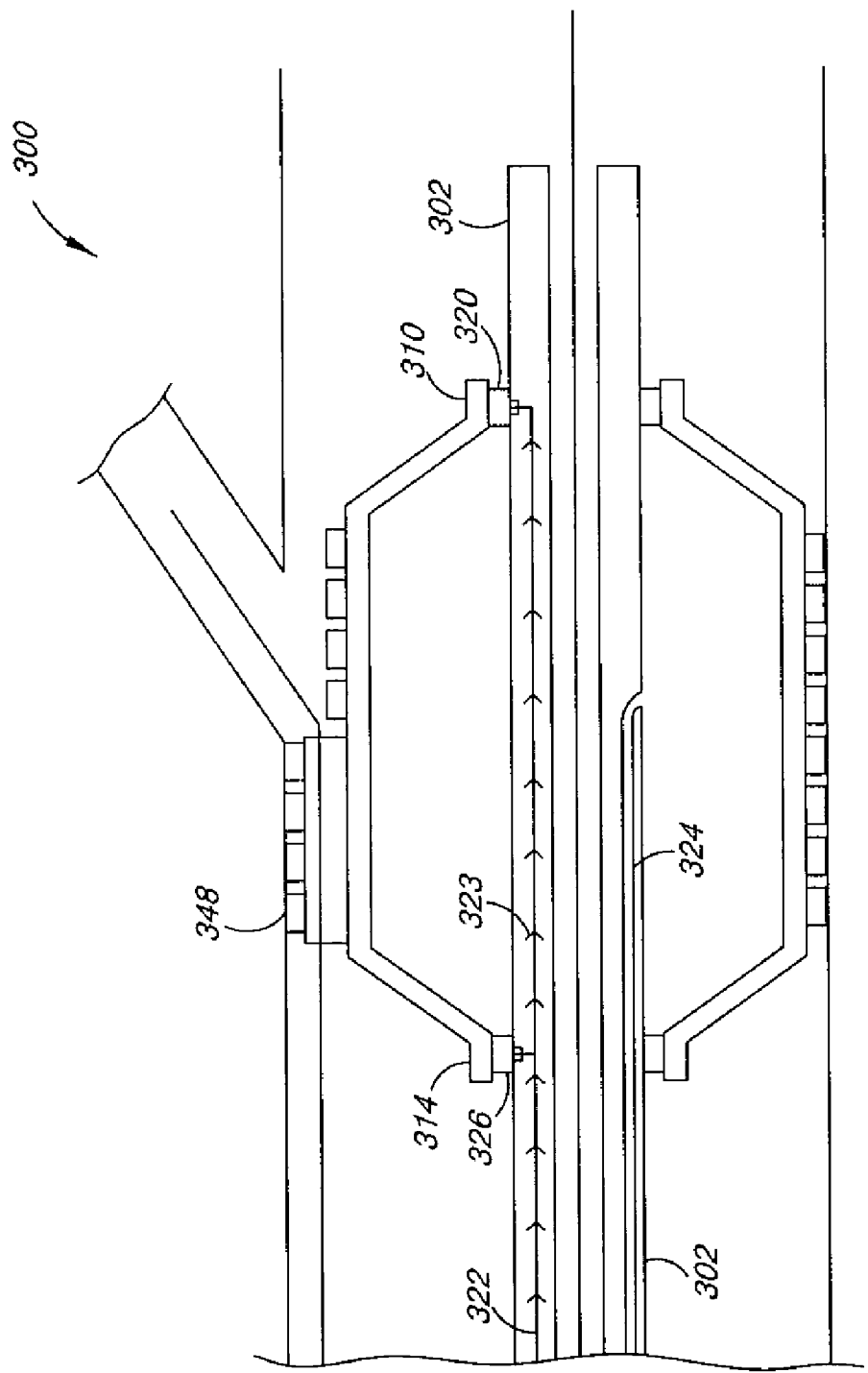

FIGS. 3A and 3B illustrate a cross-sectional view of the catheter assembly 300 including the first sealing member 320 and a second sealing member 326 coupled to the catheter shaft 302. As shown in FIGS. 3A and 3B, a second sealing member 326 can transition between a nonactivated state and an activated state in response to a temperature change in a similar manner as discussed herein with respect to the first sealing member 320. In some embodiments, the second sealing member 326 can be positioned adjacent the second balloon waist 314.

In embodiments including the first sealing member 320 and second sealing member 326, the balloon 304 can be fully rotatable with respect to the catheter shaft 302. By providing the fully rotatable balloon 304, the balloon 304 can rotate freely while the catheter assembly 300 is advanced through the vascular system to a treatment site. By allowing the balloon 304 to rotate freely, less torque is transferred from the balloon 304 to the, for example, catheter shaft 302.

As shown in FIGS. 3A and 3B, the first sealing member 320 and second sealing member 326 can be coupled to the catheter shaft 302 such that the inner diameters 328 of the first balloon waist 310 and second balloon waist 314, respectively, are larger than the exterior diameters 330 of the first sealing member 320 and second sealing member 326 in the nonactivated state. In such embodiments, the first balloon waist 310 and second balloon waist 314 are rotatable about the catheter shaft 302 when the first sealing member 320 and second sealing member 326 are in the nonactivated state.

In some embodiments, the first lead 322 can be caused to deliver current to both the first sealing member 320 and the second sealing member 326. In various embodiments, the first lead 322 can be co-extruded with the catheter shaft 302 to provide a lumen for the first lead 322 that is separate from a guidewire lumen and/or inflation lumen. The first lead lumen can also include openings to allow the first lead 322 to be electrically connected to the first sealing member 320 and the second sealing member 326. In some embodiments, the catheter assembly 300 can include a second lead to provide electric current to the second sealing member 326.

As discussed herein, the first lead 322 can provide electric current to the first sealing member 320 and second sealing member 326, causing a temperature change in the first sealing member 320 and second sealing member 326 to transition the sealing members 320, 326 from a nonactivated state, as shown in FIG. 3A, to an activated state, as shown in FIG. 3B. Once the first and second sealing members 320, 326 are transitioned into the activated state, the first and second sealing members 320, 326 can engage the first and second balloon waists 310, 314 to seal the balloon 304, thereby allowing the balloon 304 to be expanded, for example, by inflation fluid via the inflation lumen 324, as discussed herein.

Figure 4A:
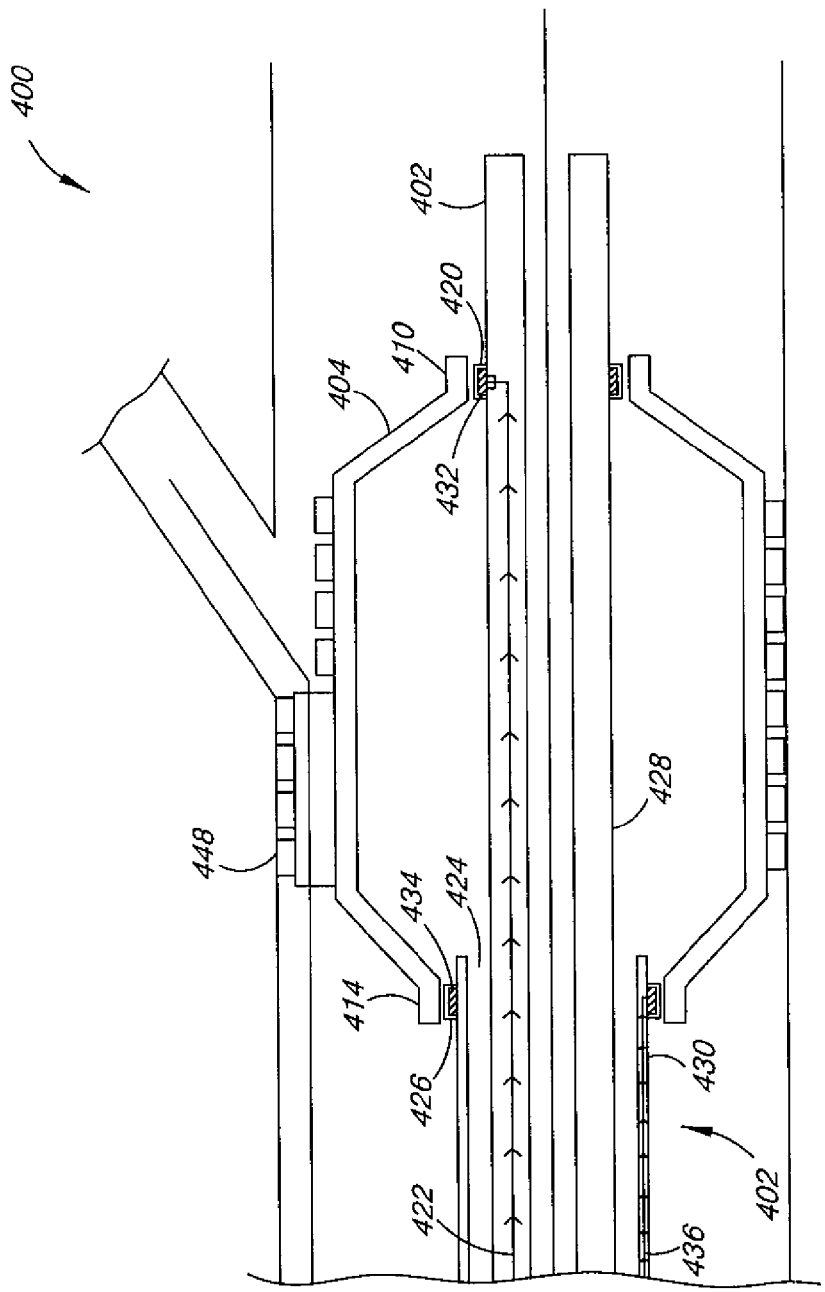
FIGS. 4A and 4B illustrate a cross-sectional view of an embodiment of the catheter assembly according to an embodiment of the present disclosure.
Figure 4B:
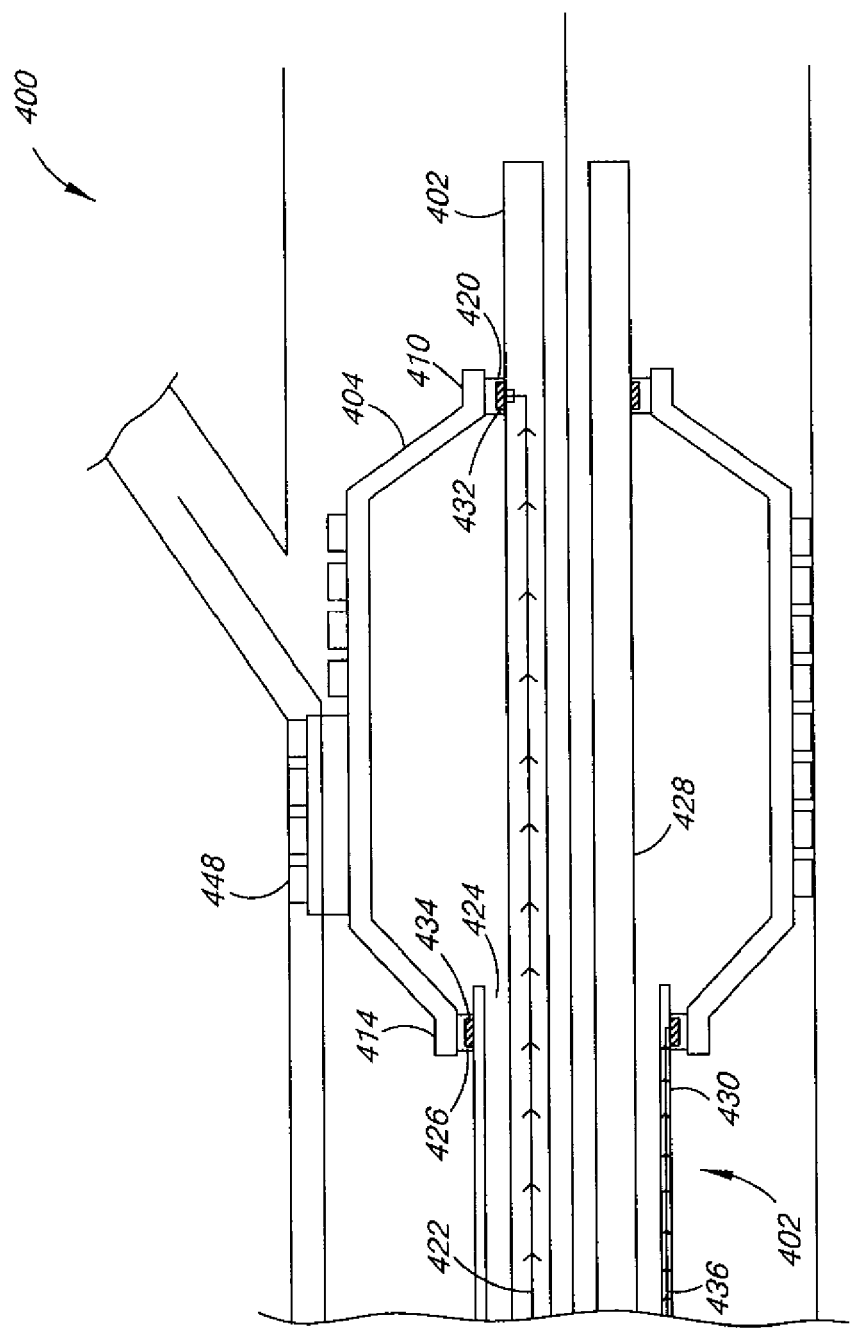

FIGS. 4A and 4B illustrate a cross-sectional view of an embodiment of the catheter assembly 400 including the first sealing member 420 and the second sealing member 426 coupled to the catheter shaft 402. In some embodiments, the catheter shaft 402 can include an inner catheter shaft 428 and an outer catheter shaft 430, where the outside surface of the inner catheter shaft 428 and the inside surface of the outer catheter shaft 430 define an inflation lumen 424. In various embodiments, the first sealing member 420 can be coupled to the inner catheter shaft 428 and the second sealing member 426 can be coupled to the outer catheter shaft 430.

In the embodiment illustrated in FIGS. 4A and 4B, the first sealing member 420 and second sealing member 426 can be coupled to a first collar 432 and a second collar 434, respectively. In various embodiments, the first collar 432 and second collar 434 can be fanned into a ring configuration and coupled to the catheter shaft 402, or the inner catheter shaft 428 and outer catheter shaft 430, respectively. The first and second sealing members 420, 426 can then be coupled to an outside surface of the first and second collars 432, 434, adjacent the first and second balloon waists 410, 414 such that the first and second sealing members 420, 426 in the nonactivated state allow the balloon 404 to rotate relative the catheter shaft 402.

In various embodiments, the first and second collars 432, 434 can be formed of a conductive material that can conduct electric current from, for example, the first lead 422 to the first and second sealing member 420, 426 to transition the first and second sealing members 420, 426 from the nonactivated state to the activated state, illustrated in FIG. 4B, as discussed herein.

In some embodiments, the first lead 422 can extend through the inner catheter shaft 428 to electrically couple to the first sealing member 420. In addition, as shown in FIGS. 4A and 4B, a second lead 436 can extend through the outer catheter shaft 430 to electrically couple to the second sealing member 426. In various embodiments, the first lead 422 can be at least partially enclosed by the inner catheter shaft 428 and the second lead 436 can be at least partially enclosed by the outer catheter shaft 430.

In some embodiments, the first and second leads 422, 436 can be used to deliver an electric current to the first and second sealing members 420, 426, respectively, to cause a temperature change in the first and second sealing members 420, 426, causing the first and second sealing members 420, 426 to transition from the nonactivated state to the activated state, as shown in FIG. 4B. As discussed herein, in the activated state, the first and second sealing members 420, 426 can engage the first and second balloon waists 410, 414 to fluidly seal the inflation balloon 404, allowing an inflation fluid to expand the balloon 404.

Figure 5A:
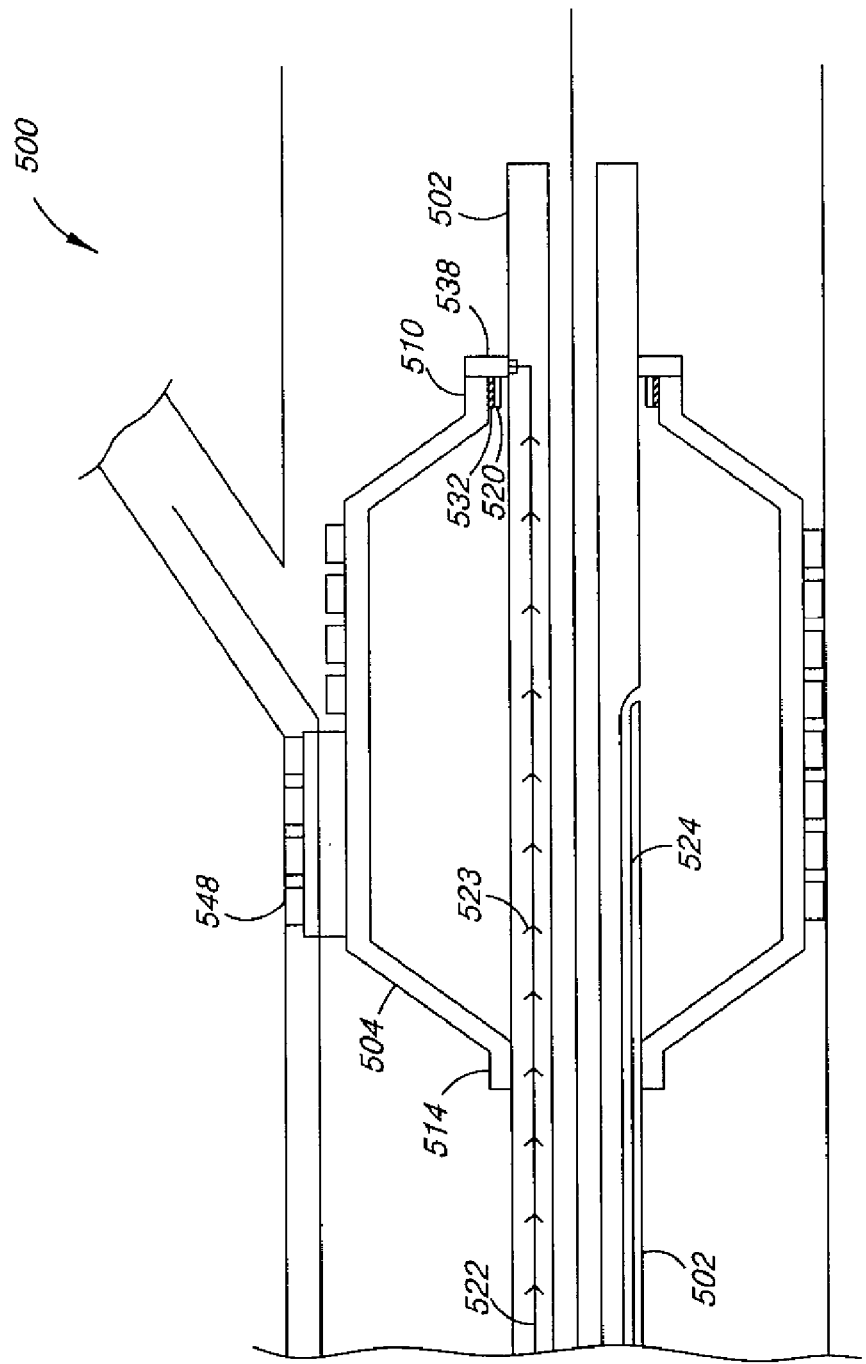
FIGS. 5A and 5B illustrate a cross-sectional view of an embodiment of the catheter assembly according to an embodiment of the present disclosure.
Figure 5B:
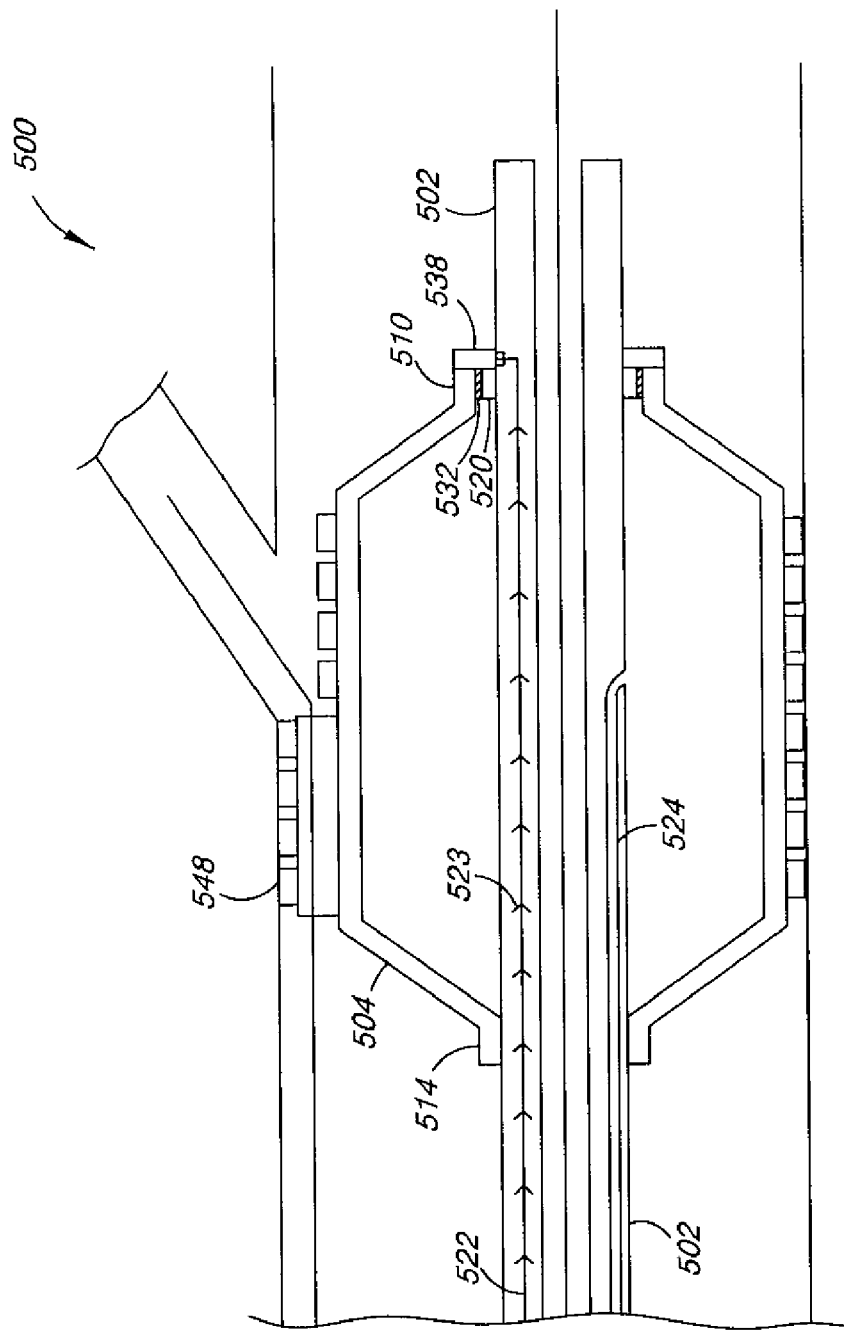

FIGS. 5A and 5B illustrate a cross-sectional view of an embodiment of the catheter assembly 500 including the first sealing member 520 coupled to the first balloon waist 510. As shown in FIGS. 5A and 5B, in some embodiments, the catheter assembly 500 can include a first fixed body 538 coupled to the catheter shaft 502. In some embodiments, the first fixed body 538 can prevent the balloon 504 from moving longitudinally with respect to the catheter shaft 502, as discussed herein.

In some embodiments, the first fixed body 538 can be formed of a conductive material. The conductive material can be formed of a biostable conductive material similar to those used in implantable electrical device circuitry. For example, conductive materials can include noble metals such as gold, platinum, and silver, non-noble metals such as copper, tin, nickel, and cobalt and titanium alloys, and non-metal conductors such as carbon. Other conductive materials are also possible.

In some embodiments, the first sealing member 520 can be coupled to the first balloon waist 510. In other embodiments, the first balloon waist 510 can include a first collar 532 encircling the catheter shaft 502. In addition, the first sealing member 520 can be coupled to the interior surface of the first collar 532, where the first collar 532 and the first sealing member 520 are constructed to rotate freely about the catheter shaft 502 in the unactivated state and to become fixed in position and engagement in the activated state. In such embodiments, the first collar 532 can be provided with a pre-current inner diameter, which is sufficiently greater than the outer diameter of the catheter shaft 502 to allow the first collar 532, and the first sealing member 520, and thus the balloon 504 engaged thereto to freely rotate about the catheter shaft 502 before exposure to the electric current.

In some embodiments, the first collar 532 can be integral with the first balloon waist 510. In such embodiments, the first collar 532 can be extruded or co-extruded with the balloon 510.

In various embodiments, the first fixed body 538 can be positioned in electrical contact with the first sealing member 520 coupled to the first balloon waist 510. For example, in the embodiment illustrated in FIGS. 5A and 5B, the first balloon waist 510 includes the first collar 532 coupled to the first balloon waist 510. The first fixed body 538 can be affixed to the catheter shaft 502 in physical contact with the first collar 532 and/or the first sealing member 520. In this way, the first fixed body 538 can conduct electric current from the first lead 522 to the first sealing member 520 directly and/or through the first collar 532 when the first lead 522 is, for example, co-extruded with the catheter shaft 502.

When the first fixed body 538 is exposed to an electric current, indicated by arrows 523, the change in temperature of the first fixed body 538 can cause a temperature change in the first sealing member 520 and/or the first collar 532, causing the first sealing member 520 to transition from the nonactivated state to the activated state, as discussed herein. As a consequence of the first sealing member 520 being sealed against the catheter shaft 502, the interior of the balloon 504 is made effectively fluid tight against the catheter shaft 502, thereby allowing the balloon 504 to be expanded such as by inflation via an inflation fluid through the inflation lumen 524.

As discussed herein with respect to FIGS. 2A and 2B, in some embodiments, the second balloon waist 514 can be affixed to the catheter shaft 502 to allow for partial rotatability of the balloon 504 with respect to the catheter shaft 502. Embodiments of the present disclosure can also include the second balloon waist 514 including a second collar and a second sealing member coupled to the second collar where a second fixed body prevents longitudinal movement of the balloon 504 and can conduct the electric current from the first lead 522 or a second lead to the second sealing member and/or the second collar.

Figure 6A:
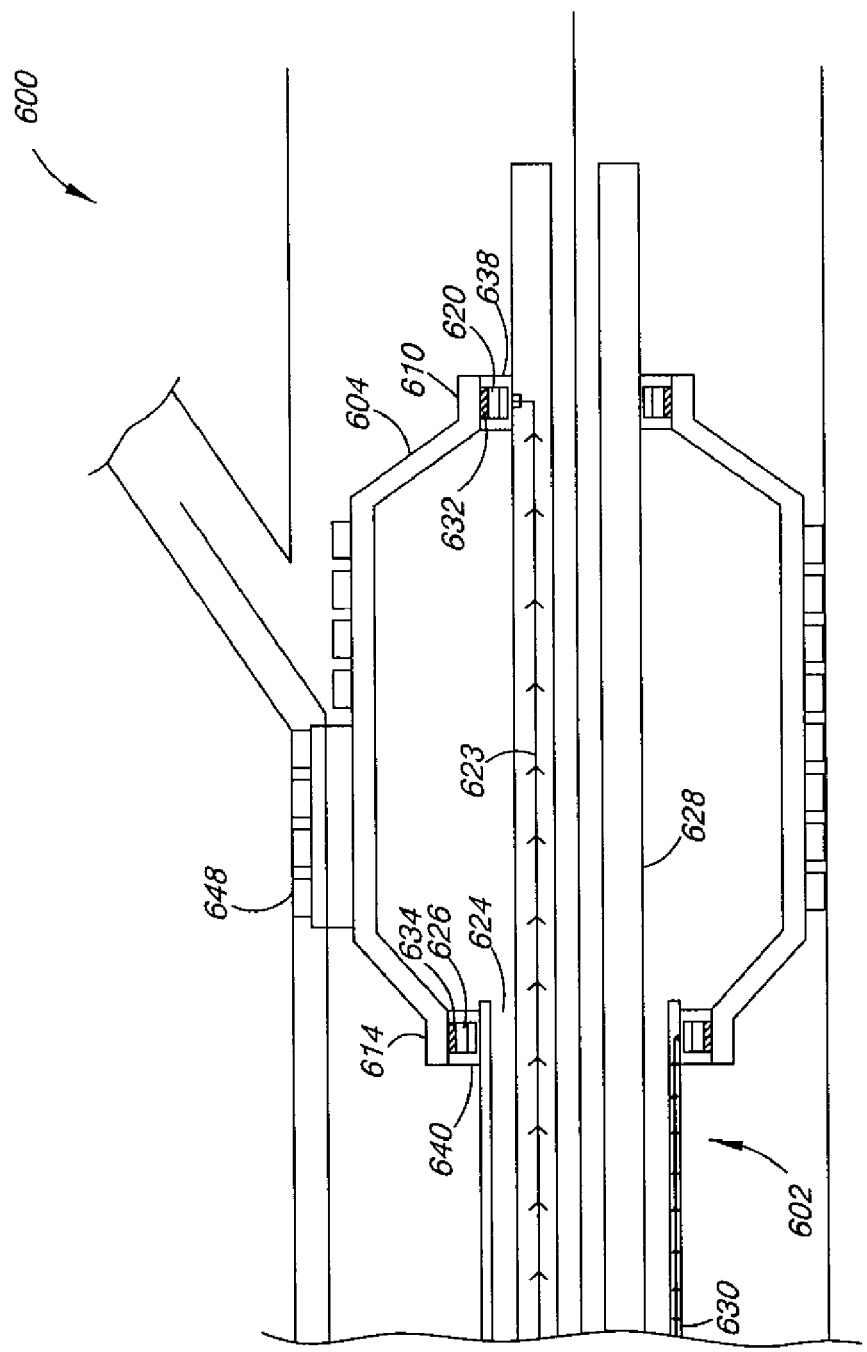
FIGS. 6A and 6B illustrate a cross-sectional view of an embodiment of the catheter assembly according to an embodiment of the present disclosure.
Figure 6B:
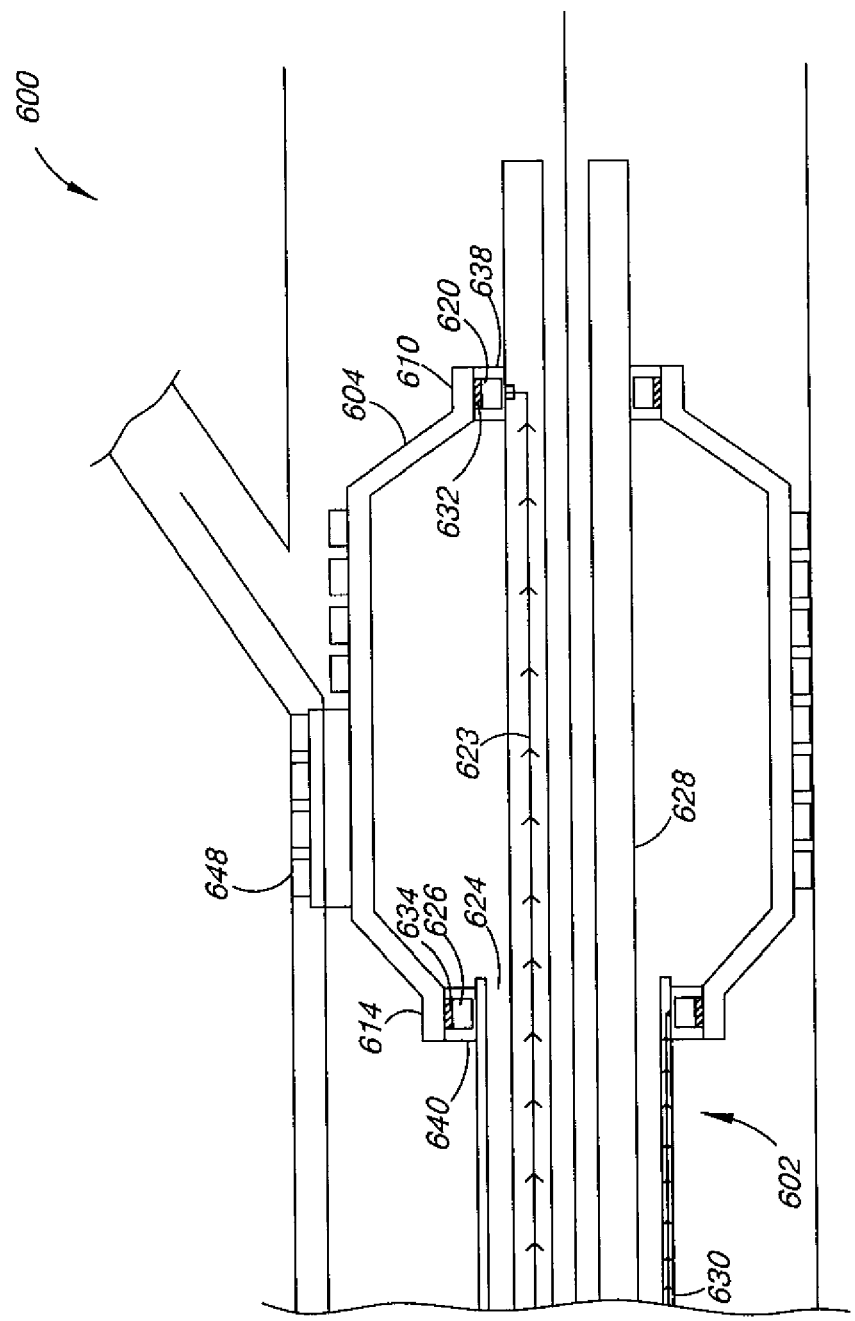

FIGS. 6A and 6B illustrate a cross-sectional view of an embodiment of the catheter assembly 600 including a first sealing member 620 and a second sealing member 626 coupled to the first balloon waist 610 and second balloon waist 614, respectively. As discussed herein, in some embodiments, the catheter shaft 602 can include an inner catheter shaft 628 and an outer catheter shaft 630. In various embodiments, the catheter shaft 628, 630 can include a first fixed body 638 and a second fixed body 640 positioned on the inner catheter shaft 628 and outer catheter shaft 630, respectively. As discussed herein, the first fixed body 638 and second fixed body 640 can prevent longitudinal movement of the balloon 604 with respect to the catheter shaft 602.

As discussed herein with respect to FIGS. 5A and 5B, in some embodiments, the first sealing member 620 and second sealing member 626 can be coupled to the first balloon waist 610 and second balloon waist 614 directly. In various embodiments, the first and second balloon waists 610, 614 can include first and second collars 632, 634 encircling the catheter shaft 602, where the first and second sealing members 620, 626 are coupled to the inside surface of the first and second collars 632, 634.

In some embodiments, the first fixed body 638 and/or second fixed body 640 can have a U-shape. In such embodiments, the first and second sealing members 620, 626 and/or the first and second collars 632, 634 can be positioned inside the U-shaped fixed bodies 638, 640 in electrical contact with the first and second fixed bodies 638, 640. In addition, the first and second fixed bodies 638, 640 can be in electrical contact with the first and second sealing members 620, 626 and/or the first and second collars 632, 634 such that the balloon 604 is able to rotate freely relative the catheter shaft 602 when the first and second sealing members 620, 626 are in the nonactivated state, as discussed herein.

When the first and second fixed bodies 638, 640 are exposed to an electric current, indicated by arrows 623, the change in temperature of the first and second fixed bodies 638, 640 can cause a temperature change in the first and second sealing members 620, 626 and/or the first and second collars 632, 634, causing the first and second sealing members 620, 626 to transition from the nonactivated state to the activated state, as discussed herein. As a consequence, the interior of the balloon 604 is made effectively fluid tight, allowing the balloon 604 to be expanded such as by inflation via an inflation fluid through the inflation lumen 624.

Figure 7A:
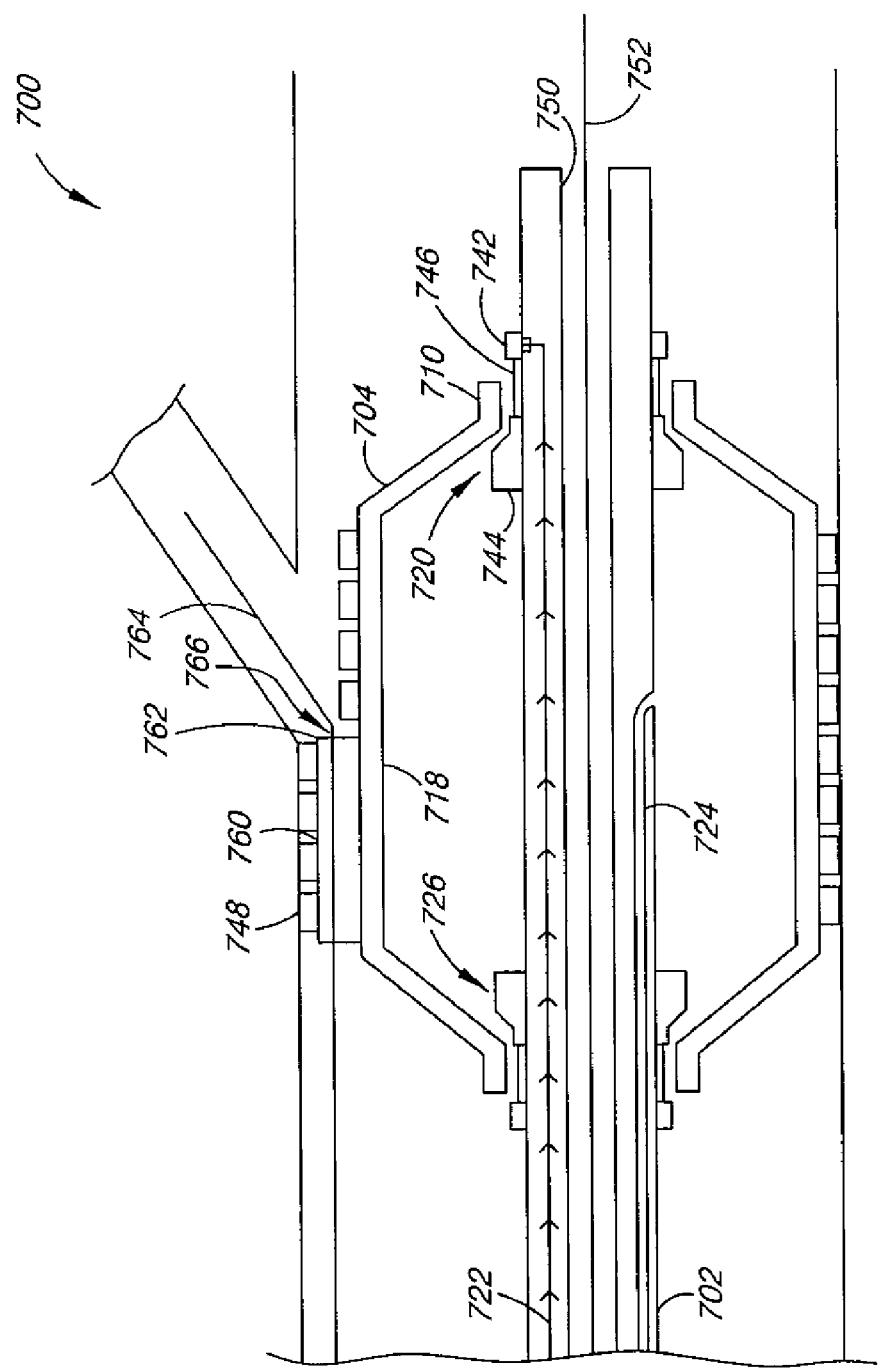
FIGS. 7A and 7B illustrate a cross-sectional view of an embodiment of the catheter assembly according to an embodiment of the present disclosure.
Figure 7B:
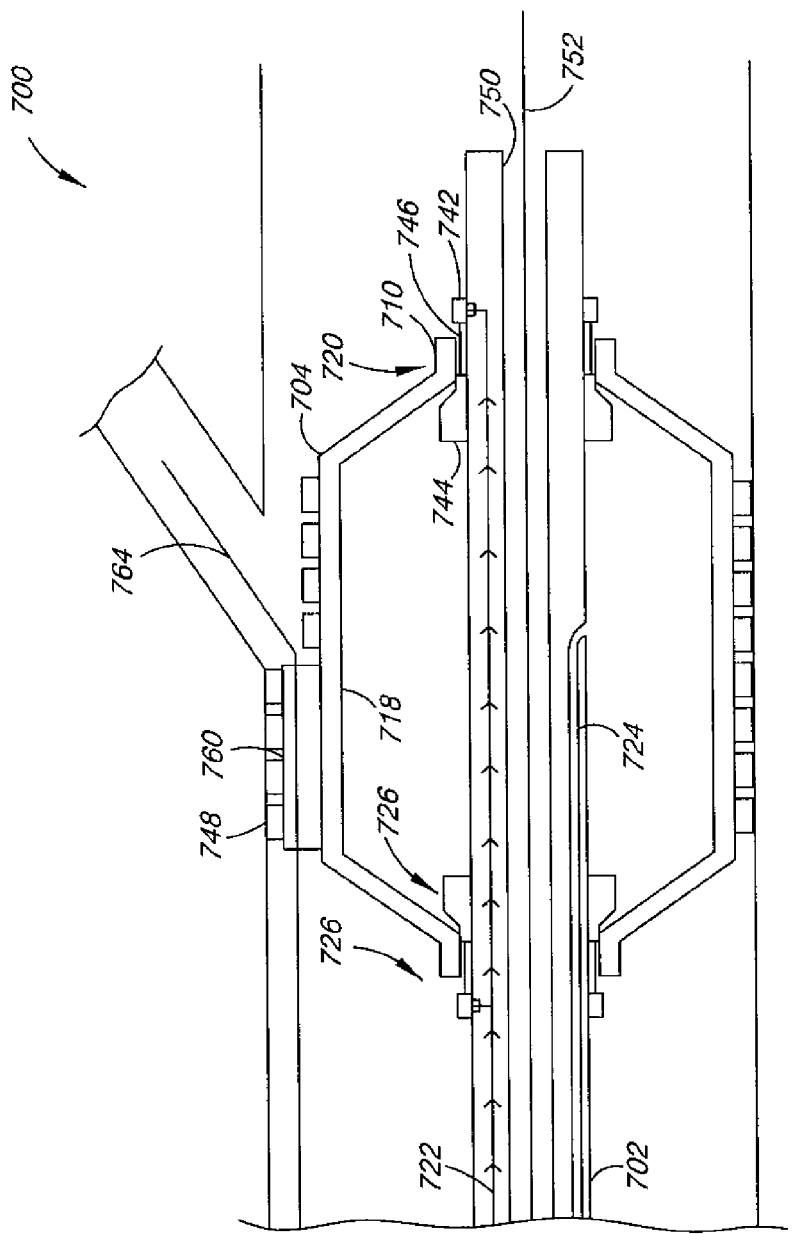

FIGS. 7A and 7B illustrate a cross-sectional view of an embodiment of the catheter assembly 700 including a first sealing member 720 and a second sealing member 726. The embodiment illustrated in FIGS. 7A and 7B illustrate the first and second sealing members 720, 726 in the form of a plug. One skilled in the art will recognize that, with respect to FIGS. 7A and 7B, the first sealing member 720 will be described, however, the description can be similarly applied to the second sealing member 726.

In some embodiments, a portion of the first sealing member 720 can be an anchor portion 742 connected to the plug portion 744 by one or more tethers 746. In such embodiments, the plug portion 744 can be positioned inside the balloon body 718 when the first sealing member 720 is in the nonactivated state so that the first balloon waist 710 can rotate freely about the catheter shaft 702.

In addition, the anchor portion 742 and plug portion 744 can encircle the catheter shaft 702 such that the plug portion 744 can move longitudinally relative the catheter shaft 702 to plug the first balloon waist 710. However, the first sealing member 720 can be restricted from rotating relative the catheter shaft 702 to prevent the tethers 746 from bending and/or twisting.

In the embodiment illustrated in FIGS. 7A and 7B, the plug portion 744 of the first sealing member 720 can be formed of a material that can form a seal with the first balloon waist 710. For example, the plug portion 744 can be formed of rubber, plastic, ceramic, and/or metal, among others, as long as the material can be affixed to the catheter assembly 700. In addition, in some embodiments, the plug portion 744, the first balloon waist 710, and/or other elements of the catheter assembly 700 can be loaded, coated, or layered with a radiopaque marker in order to verify placement and/or alignment of the catheter assembly 700.

In addition, the anchor portion 742 and tether 746 can be formed of a conductive material that can contract and/or expand in response to a temperature change. In some embodiments, the tether 746 can be formed of a conductive material that changes shape in response to a temperature change. For example, the tether 746 can change from having a rod-like shape to having a helical shape, in order to pull the plug portion 744 against the first balloon waist 710. Other configurations are also possible. In such embodiments, the tether 746 can be formed of nickel-titanium alloys (e.g., Nitinol) or other shape memory materials. In addition, the anchor portion 742 can be formed of a conductive material to conduct the electric current to the tether 746. Some exemplary conductive materials that the anchor portion 742 can be formed of can include biostable conductive materials such as noble metals, non-noble metals, and non-metal conductors, as discussed herein, and also alloys with a high content of such materials. In some embodiments, the anchor portion 742 can be formed of or be encapsulated with semi-conductive materials such as carbon, silicon, and metal oxides, among others.

In various embodiments, a first lead 722 can be connected to the first anchor portion 742 through the catheter shaft 702. When the electric current is delivered to the first anchor portion 742, a change in temperature of the first anchor portion 742 can cause the tether 746 to contract, pulling the plug portion 744 into the first balloon waist 710. By contracting the tether 746, the interior of the balloon 704 is made effectively fluid tight, allowing the balloon 704 to be expanded, such as by inflation via an inflation fluid through the inflation lumen 724.

In some embodiments, the catheter shaft 702 can include one or more bands of radiopaque material. In some embodiments, a band can be detectable by imaging modalities such as X-Ray, MRI, or ultrasound.

As shown in FIGS. 7A and 7B, and in the various embodiments shown in FIGS. 1-7, prior to electric activation of the first sealing member 720 and/or second sealing member 726, the balloon 704 or a portion of the balloon can be freely rotatable about the catheter shaft 702. This capacity to freely rotate allows a stent 748 mounted on the balloon 704 to be rotationally oriented within a body during advancement of the assembly without necessitating torquing of the catheter shaft 702, as discussed herein. Because the balloon 702 can be freely rotatable, it can be desirable to provide the balloon 704 with a mechanism which allows the balloon 704 to be rotated to a desired position.

In the various embodiments described herein, the catheter assembly 700 can be a fixed wire catheter or any other catheter design. In the embodiments illustrated for example, the catheter can be an over the wire design where the catheter shaft defines a primary guidewire lumen 750 along which a primary guidewire 752 can be advanced.

In some embodiments, such a mechanism is comprised of a secondary guidewire housing 760. The housing 760 may be comprised of a tubular member which defines a secondary guidewire lumen 762 through which a secondary guidewire 764 may be advanced. The housing 760 can be engaged to the balloon 704, for example coupled to an external surface of the balloon 704, or defined by the balloon wall as desired. The housing 760 can include one or more tubular members. Where multiple members are included in the housing 760, the members can be disposed about one another to provide the housing 760 with a variety of flexibility, hardness, and/or stiffness characteristics as desired. As such, the housing 760 may be constructed of any of a wide variety of materials including metals, polymers, rubber, silicone, multilayer materials, urethanes, Pebax, HDPE, etc.

When the stent 748 is positioned on the balloon 704, such as in the manner depicted in FIGS. 1-7, a proximal portion of the stent 748 can also be disposed about at least a portion of the secondary guidewire housing 760. When the stent 748 is thusly positioned about the balloon 704 and the housing 760, in some embodiments, at least a portion of the housing 760 and/or the secondary guidewire 764 extends distally through a cell opening 766 of the stent 748.

The stent 748 may be a stent as is shown in FIG. 1, which is at least partially constructed of a plurality of interconnected struts, connectors, or members. The stent 748 can define a proximal opening, a distal opening, and a flow path therebetween. The cell openings are in fluid communication with the flow path. As used herein, a "cell opening" is an opening in the stent 748 defined by the interconnected struts, connectors, or members.

The secondary guidewire 764 and/or the secondary guidewire housing 760 can be threaded through one of the cell openings 766 when the stent 748 is positioned onto the assembly 700. In such embodiments, the members that define the cell opening 766, as well as the shape of the cell opening 766 through which the secondary guidewire 764 exits the stent 748, may be distorted or modified in order to accommodate the passage of secondary guidewire 764 and/or the secondary guidewire housing 760 there through. This modified cell opening 766 can be positioned on the stent 748 between the proximal opening and the distal opening.

It should be noted that when the stent 748 is placed on the balloon 704 in the manner described above, the distortion of the cell opening 766 and the adjacent members may be of a minimal nature providing only a sufficient alteration to the cell to allow sliding passage of the secondary guidewire 764, and if desired a distal portion of the secondary guidewire housing 760 there through. As such, the actual size of the cell opening 766 may be substantially similar, or only marginally different than that of the surrounding cell openings.

It should also be further noted that while stent 748 may be a standard "single vessel" stent 748 that is provided with a cell opening 766 in the manner described above, the stent 748 may also be a bifurcated stent having a trunk and/or stem portion, with one or more leg portions and/or branch openings adjacent thereto, through which the secondary guidewire 764 may be passed. Such bifurcated stents and stent assemblies are well known in the art.

In some embodiments, the secondary guidewire 764 is merely slid between the balloon 704 and the stent 748 without the use of a housing 760. In some embodiments, where the stent 748 is to be positioned substantially proximal to a side branch of the bifurcation, the secondary guidewire 764 and/or housing 760 may be configured to extend under the entire length of the stent 748.

In operation, the secondary guidewire 764 can be initially advanced through a vessel and into a side branch of a bifurcation. By advancing the catheter assembly 700 along the secondary guidewire 764 in the manner described above, the balloon 704 and the stent 748 disposed thereabout will be rotated to align the secondary opening of the stent 748 with the side branch vessel. Once properly positioned in this manner the first and/or second sealing members 720, 726 can be activated and the balloon 704 expanded to deliver the stent 748. As one skilled in the art will appreciate, once the stent 748 is delivered the balloon 704 can be deflated and the assembly 700 can be withdrawn.

In some embodiments, the stent 748, and/or one or more portions of the assembly 700 thereof, may be configured to deliver one or more therapeutic agents to a delivery site within the vessel or one or more areas adjacent thereto.

To better accommodate placement of a therapeutic agent on the stent 748, in some instances one or more stent members may be configured to include one or more holes, notches, or other surface features to which one or more therapeutic agents may be placed for delivery to the aneurysm site. A therapeutic agent may be placed on the stent 748 in the form of a coating. Often the coating can include at least one therapeutic agent and at least one polymer.

A therapeutic agent may be a drug, a non-genetic agent, a genetic agent, etc. Some examples of suitable non-genetic therapeutic agents include but are not limited to: anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vascoactive mechanisms, and any combinations thereof.

An agent can include a genetic therapeutic agent, such a genetic agent may include but is not limited to: anti-sense DNA and RNA; DNA coding for anti-sense RNA, tRNA or rRNA to replace defective or deficient endogenous molecules; angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor a, hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7; dimeric proteins such as homodimers, heterodimers, or combinations thereof, alone or together with other molecules; molecules capable of inducing an upstream or downstream effect of a BMP such as "hedgehog" proteins, or the DNA's encoding them and any combinations thereof.

A therapeutic can include cellular material, the cellular material may include but is not limited to: cells of human origin (autologous or allogeneic); cells of non-human origin (xenogeneic) and any combination thereof. Some examples of cellular material include but are not limited to the following:

SP—(side population cells) These cells are thought to be some of the most primitive adult stem cells. They are isolated by a specific FACS technique utilizing the ability of SP cells to exclude Hoechst dye from the nucleus. In addition to bone marrow, SP cells have been isolated from most tissues, including: cardiac and skeletal muscle. By the more common surface protein identification these cells are $Lin^-$, $Sca-1^+$, $c-Kit^+$, $CD43^+$, $CD45^+$, $CD34^-$.

$Lin^-$—(lineage negative cells) This group of cells is isolated from the bone marrow and all cells which have differentiated to a specific lineage (e.g. red blood cells) have been removed, leaving all of the stem and progenitor cells. This is beneficial because all primitive cells remain, but may reduce efficiency by including irrelevant, primitive cell types.

$Lin^-CD34^-$—Although $CD34^+$ cells have received much attention, many articles have been published lately which suggest the most primitive bone marrow derived stem cells are $CD34^-$.

Lin⁻CD34⁺—Presence of the cell surface protein CD34 has been used to identify hematopoietic stem cells. However, the marker is also present on progenitor cells and white blood cells of various levels of maturity.

Lin⁻cKit⁺—cKit is the cell surface receptor for stem cell factor, and therefore a logical choice for stem cell selection. Most widely studied from bone marrow sources, but have also been isolated from the heart.

MSC—(mesenchymal stem cells) Named so because ordinarily these cells differentiate into cells of mesenchymal tissues (e.g. bone, cartilage, fat), but may also differentiate into cardiomyocytes under certain conditions. Easily isolated from bone marrow and, unlike hematopoietic stem cells, proliferate in vitro. A subpopulation of MSCs has been shown to self-renew faster and have a greater potential for multipotential differentiation than the general MSC population.

Cord Blood Cells—Derived from the blood remaining in the umbilical vein following child birth. This blood has been shown to contain a higher percentage of immature stem cells or progenitor cells. Typically, a matched donor must be found for patients, but a lower incidence of graft versus host disease compared to stem cell isolation from adult blood has been reported. Disadvantages include: insufficient cell number in small blood volumes, unforeseen congenital defects, and contamination by mother's blood which is likely not HLA matched.

Cardiac or other tissue derived stem cells—Most work to date has focused on isolating stem cells from bone marrow. This is due to extensive work in improving bone marrow transplants for chemotherapy and leukemia treatments. However, there is evidence that similar stem cells which can be identified by similar means (e.g. SP, cKit) can be isolated from other tissues (e.g. fat, cardiac muscle).

Whole bone marrow—An "it's in there" approach where whole bone marrow (filtered for bone particles) is transplanted. Benefits include: little processing, all stem and progenitor cells are present, and matrix proteins and growth factors may also be present. Downside—if one or two stem cell types are responsible for cardiac improvement they will only be present in very low numbers.

BM-MNCs—(bone marrow mononuclear cells) Separated from whole bone marrow by a density gradient centrifugation procedure, this population contains non-granular white blood cells, progenitor cells, and stem cells.

EPCs—(endothelial progenitor cells) Isolated from bone marrow based on cell surface markers, these cells will become endothelial cells. In theory, these cells will form new blood vessels when delivered to ischemic tissue.

Skeletal myoblasts—(or satellite cells) These cells are responsible for the regeneration of skeletal muscle following injury. They have the ability to fuse with other myoblasts or damaged muscle fibers. Cardiac muscle therapies assume these cells can integrate into the host tissue and improve tissue properties or functionally participate in contraction.

MDCs—(muscle derived cells) A population of cells isolated from adult skeletal muscle which are similar to myoblasts. The isolation technique preplating entails collecting cells which attach to culture dishes at different times after biopsy. Cells with the best potential plate in the 6$^{th}$ group and takes several days to obtain. Investigators working with these cells claim they are a refined population of myoblasts and should result in higher engraftment efficiencies and efficacious procedures.

Go cells—Recently isolated from adult skeletal muscle, these non-satellite cells express GATA-4 and, under certain in vitro growth conditions, progress to spontaneously beating cardiomyocyte-like cells.

Endothelial cells—Transplantation of autologous endothelial cells along with a fibrin matrix induced angiogenesis and improved cardiac function in an ischemic sheep model.

Adult cardiomyocytes Fibroblasts—Easily obtained from adult tissues, fibroblasts may provide growth factors or participate in the would healing response. Fibroblast play a critical role in wound healing; the synthesis and deposition of extracellular matrix. Fibroblasts commonly become contractile in wound healing environments.

Smooth muscle cells—Isolated from arteries, these cells may participate or encourage angiogenesis and/or beneficial cardiac remodeling following MI.

MSCs+5-aza—Culture of mesenchymal stem cells with 5-aza forces differentiation into cardiomyocytes. These cells beat spontaneously after treatment.

Adult cardiac fibroblasts+5-aza—In theory, in vitro treatment of cardiac fibroblasts with 5-aza will result in differentiation into myogenic cells.

Genetically modified cells—Isolation of cells from the patient and genetically modifying them in vitro to encourage production of proteins or differentiation into a cell type which will be beneficial for treating heart failure.

Tissue engineered grafts—Isolation of cells from the patient which are then seeded onto and cultured within resorbable scaffolds (e.g. collagen, PLGA). These cell seeded constructs are then implanted into the patient.

MyoD scar fibroblasts—MyoD family of transcription factors prompt skeletal muscle cell differentiation in fibroblasts. Procedure involves isolation of cardiac scar fibroblasts, genetic transfection with MyoD in vitro and delivery of the cells to the heart to encourage myogenesis.

Pacing cells—Genetically modified fibroblasts which become electrically conducting and signal generators.

Embryonic stem cell clones—Use of cloning technology to produce cardiomyocytes, progenitors, or stem cells which are genetically identical to the patient.

Embryonic stem cells—These cells are the most primitive of cells and will differentiate into functional cardiomyocytes under certain conditions. Both political and technological hurdles must be overcome before commercialization of this technology.

Fetal or neonatal cells—Isolated from the heart of donors, these cells may incorporate into host tissue without immune rejection. Some cardiomyocyte progenitor cells must be present due to the continued growth of the heart in fetal and neonatal humans.

Immunologically masked cells—Allogeneic cell sources (e.g. donor cardiomyocytes) are currently unfeasible due to immune rejection. However, masking technologies have been developed which could make this technology feasible.

Tissue engineered grafts—Isolation of cells from a donor which are then seeded onto and cultured within resorbable scaffolds (e.g. collagen, PLGA). These cell seeded constructs are then implanted into the host or recipient.

Genetically modified cells—Isolation of cells from a donor and genetically modifying them in vitro to encourage production of proteins or differentiation into a cell type which will be beneficial for treating heart failure. The modified cells will then be transplanted into the host or patient.

Teratoma derived cells—A teratocarcinoma is a form of cancer in which the tumor is composed of a heterogeneous mixture of tissues. Through isolation of cells from this tumor and in vitro manipulation and culture a neuronal cell line has been developed. Layton Biosciences has successfully used these cells to form new brain tissue in stroke patients. Similar techniques may be used to produce a myogenic cell line.

Where a therapeutic agent comprises at least one polymer agent or coating, the at least one coating may include but is not limited to: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.), fibrin, collagen and derivatives thereof; polysaccharides such as celluloses, starches, dextrans, alginates and derivatives; hyaluronic acid; squalene emulsions; polyacrylic acid, a copolymer of polylactic acid and polycaprolactone; medical-grade biodegradable materials such as PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO$_4$'s; cyanoacrylate; 50/50 DLPLG; polydioxanone; polypropylene fumarate; polydepsipeptides; macromolecules such as chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; and any combinations thereof.

In some instances a suitable polymer agent or coating comprises block copolymers comprising at least one A block and at least one B block. The A blocks are preferably soft elastomeric blocks, which are based upon one or more polyolefins, or other polymer with a glass transition temperature at or below room temperature. For example, the A blocks can be polyolefinic blocks having alternating quaternary and secondary carbons of the general formulation:—(CRR'—CH$_2$)$_n$—, where R and R' are, independently, linear or branched aliphatic groups such as methyl, ethyl, propyl, isopropyl, butyl, isobutyl and so forth, or represent cyclic aliphatic groups such as cyclohexane, cyclopentane, and the like, either with or without pendant groups. Preferred polyolefinic blocks include polymeric blocks of isobutylene,

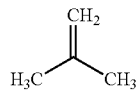

(i.e., polymers where R and R' are methyl groups). Other examples of A blocks include silicone rubber blocks and acrylate rubber blocks.

The B blocks are preferably hard thermoplastic blocks with glass transition temperatures significantly higher than the elastomeric A blocks which, when combined with the soft A blocks, are capable of, inter alia, altering or adjusting the hardness of the resulting copolymer to achieve a desired combination of qualities. Examples of B blocks include polymers of methacrylates or polymers of vinyl aromatics. More specific examples of B blocks include blocks that are (a) formed from monomers of styrene

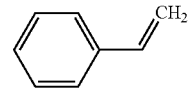

styrene derivatives (e.g., x-methylstyrene, ring-alkylated styrenes or ring-halogenated styrenes or other substituted styrenes where one or more substituents are present on the aromatic ring) or mixtures of the same, collectively referred to herein as "styrenic blocks" or "polystyrenic blocks" or are (b) formed from monomers of methylmethacrylate, ethylmethacrylate, hydroxyethyl methacrylate or mixtures of the same.

The block copolymers can be provided in a variety of architectures, including cyclic, linear, and branched architectures. Branched architectures include star-shaped architectures (e.g., architectures in which three or more chains emanate from a single region), comb architectures (e.g., copolymers having a main chain and a plurality of side chains), and dendritic architectures (including arborescent or hyperbranched copolymers).

Some specific examples of such block copolymers include the following: (a) BA (linear diblock), (b) BAB or ABA (linear triblock), (c) B(AB)$_n$ or A(BA)$_n$ (linear alternating block), or (d) X-(AB)$_n$ or X—(BA)$_n$ (includes diblock, triblock and other radial block copolymers), where n is a positive whole number and X is a starting seed, or initiator, molecule. One specific group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block, with the triblock therefore denoted as BAB). A particularly beneficial polymer from this group is polystyrene-polyisobutylene-polystyrene triblock copolymer (SIBS). Where n=3 or more, these structures are commonly referred to as star-shaped block copolymers. Other examples of block polymers include branched block copolymers such as dendritic block copolymers, wherein at least one of the A and B blocks is branched, for instance, where the A blocks are branched and are capped by the B blocks.

While the present invention has been shown and described in detail above, it will be clear to the person skilled in the art that changes and modifications may be made without departing from the spirit and scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled. In addition, one of ordinary skill in the art will appreciate upon reading and understanding this disclosure that other variations for the invention described herein can be included within the scope of the present invention.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A catheter assembly, comprising:
a catheter shaft;
a balloon positioned on the catheter shaft, where the balloon has a first balloon waist;
a first lead extending longitudinally through the catheter shaft;
a first fixed body affixed to the catheter shaft, where the first fixed body prevents the balloon from moving longitudinally with respect to the catheter shaft, and where the first fixed body is a conductive material and is coupled to the first lead; and
a first sealing member adjacent the first balloon waist, where the first sealing member includes a metal that expands in response to a temperature change and the first lead provides electrical current via the first fixed body to reversibly transition the first sealing member from a nonactivated state to an activated state in response to the temperature change in the first sealing member, and where at least a portion of the balloon rotates relative the catheter shaft in the nonactivated state and the first sealing member engages the catheter shaft to form a fluid tight seal and to prevent rotation of the balloon relative the catheter shaft in the activated state.

2. The catheter assembly of claim 1, where the first sealing member is coupled to the balloon waist.

3. The catheter assembly of claim 1, further including a second balloon waist and a second sealing member adjacent the second balloon waist and coupled to the first lead, where the second sealing member includes a metal that expands in response to a temperature change and the first lead provides electrical current via a second fixed body that is affixed to the catheter shaft and is a conductive material to reversibly transition the second sealing member from the nonactivated state to the activated state in response to the temperature change in the second sealing member, where the balloon rotates relative to the catheter shaft in the nonactivated state and the second sealing member engages the second balloon waist to form a fluid tight seal and to prevent rotation of the balloon relative to the catheter shaft in the activated state.

4. The catheter assembly of claim 1, further including a second balloon waist and a second sealing member adjacent the second balloon waist and coupled to a second lead, where the second sealing member includes a metal that expands in response to a temperature change and the second lead provides electrical current via a second fixed body that is a conductive material that is affixed to the catheter shaft and coupled to the second lead to reversibly transition the second sealing member from the nonactivated state to the activated state in response to the temperature change in the second sealing member, where the balloon rotates relative the catheter shaft in the nonactivated state and the second sealing member engages the second balloon waist to form a fluid tight seal and to prevent rotation of the balloon relative the catheter shaft in the activated state.

5. The catheter assembly of claim 1, where the first sealing member in the activated state has a diameter in a range of approximately 0.5 percent to 20 percent larger than the diameter of the first sealing member in the nonactivated state.

6. The catheter assembly of claim 1, including a secondary guidewire housing including a substantially tubular member engaged to the balloon, the secondary guidewire housing defining a secondary guidewire lumen through which a secondary guidewire may be slidingly positioned.

7. The catheter assembly of claim 6, where the secondary guidewire housing is coupled to an external surface of the balloon.

8. The catheter assembly of claim 1, including a balloon expandable stent disposed about at least a portion of the balloon, where at least a proximal portion of the stent overlays at least a portion of the secondary guidewire housing.

9. A catheter assembly, comprising:
a catheter shaft;
a balloon positioned on the catheter shaft, where the balloon has a first balloon waist that includes a first collar encircling the catheter shaft;
a first sealing member coupled to the first collar, where the first sealing member expands in response to a temperature change;
a first lead extending longitudinally through the catheter shaft; and
a first fixed body affixed to the catheter shaft, where the first fixed body prevents the balloon from moving with respect to the catheter shaft in a first longitudinal direction and where the first fixed body is a conductive material and is coupled to the first lead to provide electrical current via the first fixed body to reversibly transition the first sealing member from a nonactivated state to an activated state in response to the temperature change.

10. The catheter assembly of claim 9, where the balloon rotates relative the catheter shaft in the nonactivated state and the first sealing member engages the catheter shaft to form a fluid tight seal and prevents rotation of the balloon relative the catheter shaft in the activated state.

11. The catheter assembly of claim 9, where the first sealing member expands to engage the catheter shaft to form the fluid tight seal and to prevent rotation of the balloon relative the catheter shaft.

12. The catheter assembly of claim 9, where the first fixed body provides the electric current to the first collar.

13. The catheter assembly of claim 9, where the first collar is integral with the first balloon waist.

14. The catheter assembly of claim 9, where the first fixed body is a U-shaped ring coupled to the catheter shaft adjacent the first collar.

15. The catheter assembly of claim 9, where the balloon has a second balloon waist, and the catheter assembly includes:
a second collar coupled to the second balloon waist and encircling the catheter shaft;
a second fixed body coupled to the catheter shaft adjacent the second collar; and
a second sealing member coupled to the second collar and in electrical contact with the second fixed body, where the first lead provides electrical current to the second sealing member through the second fixed body to reversibly transition the second sealing member from a nonactivated state to an activated state in response to a temperature change in the second sealing member, and where at least a portion of the balloon rotates relative the catheter shaft in the nonactivated state and the second sealing member engages the catheter shaft to form a fluid tight seal and to prevent rotation of the balloon relative the catheter shaft in the activated state.

16. The catheter assembly of claim 15, where the second fixed body prevents the balloon from moving with respect to the catheter shaft in a second longitudinal direction.

17. The catheter assembly of claim 9, where the balloon has a second balloon waist, and the catheter assembly includes:

a second lead extending longitudinally through the catheter shaft;

a second collar coupled to the second balloon waist and encircling the catheter shaft; and a second fixed body coupled to the catheter shaft adjacent the second collar; and a second sealing member coupled to the second collar and in electrical contact with the second fixed body, where the second lead provides electrical current to the second sealing member through the second fixed body to reversibly transition the second sealing member from a nonactivated state to an activated state in response to a temperature change in the second sealing member, and where at least a portion of the balloon rotates relative the catheter shaft in the nonactivated state and the second sealing member engages the catheter shaft to form a fluid tight seal and to prevent rotation of the balloon relative the catheter shaft in the activated state.

18. A catheter assembly, comprising:

a catheter shaft;

a balloon positioned on the catheter shaft, where the balloon has a first balloon waist;

a first lead extending longitudinally through the catheter shaft;

a first fixed body affixed to the catheter shaft and coupled to the first lead, where the first fixed body prevents the balloon from moving longitudinally with respect to the catheter shaft; and a first sealing member adjacent the first balloon waist, where the first sealing member reversibly transitions from a nonactivated state, where at least a portion of the balloon rotates relative the catheter shaft, to an activated state that prevents rotation of the balloon relative the catheter shaft.

19. The catheter assembly of claim 18, where in the activated state the first sealing member engages the catheter shaft to form a fluid tight seal.

20. The catheter assembly of claim 18, where the first sealing member includes a metal that expands in response to a temperature change and the first lead provides electrical current via the first fixed body to the first sealing member.

* * * * *